(12) United States Patent
Semones

(10) Patent No.: US 7,005,434 B2
(45) Date of Patent: Feb. 28, 2006

(54) COMPOUNDS AND USES THEREOF

(75) Inventor: Marcus A. Semones, King of Prussia, PA (US)

(73) Assignee: SB Corporation, Philadelphia, PA (US)

( * ) Notice: Subject to any disclaimer, the term of this patent is extended or adjusted under 35 U.S.C. 154(b) by 0 days.

(21) Appl. No.: 10/466,585

(22) PCT Filed: Jan. 18, 2002

(86) PCT No.: PCT/US02/01474

§ 371 (c)(1),
(2), (4) Date: Jul. 18, 2003

(87) PCT Pub. No.: WO02/060382

PCT Pub. Date: Aug. 8, 2002

(65) Prior Publication Data

US 2004/0048888 A1    Mar. 11, 2004

Related U.S. Application Data

(60) Provisional application No. 60/262,862, filed on Jan. 19, 2001.

(51) Int. Cl.
C07D 471/06    (2006.01)
A61K 31/495    (2006.01)

(52) U.S. Cl. ...................... 514/300; 546/122
(58) Field of Classification Search ................. 546/122; 514/300
See application file for complete search history.

(56) References Cited

U.S. PATENT DOCUMENTS 5,945,431 A * 8/1999 Jin et al. ..................... 514/300
6,025,489 A    2/2000 Davey et al.

FOREIGN PATENT DOCUMENTS

| WO | WO 96/15128 | 5/1996 |
| WO | WO 97/34894 | 9/1997 |
| WO | WO 99/09030 | 2/1999 |
| WO | WO 99/29318 | 6/1999 |
| WO | WO 96/61444 | 12/1999 |

OTHER PUBLICATIONS

Thompson, A.M., et al., "3-(3,5-Dimethoxyphenyl)-1,6-Naptthyridine-2,7-diamines and related 2-urea derivatives are potent and selective inhibitors of the FGF receptor-1 tyrosone kinase", (2000), J. Med. Chem., vol. 43, pp. 4200-4211.

* cited by examiner

Primary Examiner—Zinna Northington Davis
(74) Attorney, Agent, or Firm—James C. Kellerman; Stephen Venetianer; Charles M. Kinzig

(57) ABSTRACT

The present invention relates to novel compounds and the treatment of mammalian diseases in which inappropriate, excessive or undesirable angiogenesis has occurred and/or where excessive Tie2 receptor activity has occurred.

15 Claims, No Drawings

COMPOUNDS AND USES THEREOF

CROSS REFERENCES TO RELATED APPLICATIONS

This application is a National Stage Application filed under 35 U.S.C. §371 of PCT/US02/01474, filed on Jan. 18, 2002, which claims priority of U.S. Provisional Application No. 60/262,862, filed Jan. 19, 2001.

FIELD OF THE INVENTION

The present invention relates to the treatment of diseases, in a mammal, in which inappropriate, excessive or undesirable angiogenesis has occurred and/or where excessive Tie2 receptor activity has occurred.

BACKGROUND OF THE INVENTION

Chronic proliferative diseases are often accompanied by profound angiogenesis, which can contribute to or maintain an inflammatory and/or proliferative state, or which leads to tissue destruction through the invasive proliferation of blood vessels. (Folkman, EXS 79:1–8, 1997; Folkman, *Nature Medicine* 1:27–31, 1995; Folkman and Shing, *J. Biol. Chem.* 267:10931, 1992).

Angiogenesis is generally used to describe the development of new or replacement blood vessels, or neovascularisation. It is a necessary and physiological normal process by which the vasculature is established in the embryo. Angiogenesis does not occur, in general, in most normal adult tissues, exceptions being sites of ovulation, menses and wound healing. Many diseases, however, are characterized by persistent and unregulated angiogenesis. For instance, in arthritis, new capillary blood vessels invade the joint and destroy cartilage (Colville-Nash and Scott, *Ann. Rheum. Dis.*, 51, 919,1992). In diabetes (and in many different eye diseases), new vessels invade the macula or retina or other ocular structures, and may cause blindness (Brooks et al., *Cell,* 79, 1157, 1994). The process of atherosclerosis has been linked to angiogenesis (Kahlon et al., *Can. J. Cardiol.* 8, 60, 1992). Tumor growth and metastasis have been found to be angiogenesis-dependent (Folkman, *Cancer Biol,* 3, 65, 1992; Denekamp, *Br. J. Rad.* 66, 181, 1993; Fidler and Ellis, *Cell,* 79, 185, 1994).

The recognition of the involvement of angiogenesis in major diseases has been accompanied by research to identify and develop inhibitors of angiogenesis. These inhibitors are generally classified in response to discrete targets in the angiogenesis cascade, such as activation of endothelial cells by an angiogenic signal; synthesis and release of degradative enzymes; endothelial cell migration; proliferation of endothelial cells; and formation of capillary tubules. Therefore, angiogenesis occurs in many stages and attempts are underway to discover and develop compounds that work to block angiogenesis at these various stages.

There are publications that teach that inhibitors of angiogenesis, working by diverse mechanisms, are beneficial in diseases such as cancer and metastasis (O'Reilly et al., *Cell,* 79, 315, 1994; Ingber et al., *Nature,* 348, 555, 1990), ocular diseases (Friedlander et al., *Science,* 270, 1500, 1995), arthritis (Peacock et al., *J. Exp. Med.* 175, 1135, 1992; Peacock et al., *Cell. Immun.* 160, 178, 1995) and hemangioma (Taraboletti et al., *J. Natl. Cancer Inst.* 87, 293, 1995).

Angiogenesis signals result from the interaction of specific ligands with their receptors. The Tie1 and Tie2 receptors are single-transmembrane, tyrosine kinase receptors (Tie stands for Tyosine kinase receptors with immunoglobulin and EGF homology domains). Both were recently cloned and reported by several groups (Dumont et al., *Oncogene* 8:1293–1301, 1993; Partanen et al., Mol. Cell Biol. 12:1698–1707, 1992; Sato et al., *Proc. Natl. Acad. Sci. USA* 90:9355–9358, 1993).

The Tie receptors are proteins of approximately 125 kDa, with a single putative transmembrane region. The extracellular domain of these receptors is divided into several regions: there are 3 regions that have a pattern of cysteine expression found in EGF-like domains; there are 2 regions that have some weak homology to and structural characteristics of immunoglobulin-like domains; and there are 3 regions with homology to the fibronectin III repeat structure. This particular combination of extracellular domains is unique to the Tie receptors. The intracellular portion of Tie2 is most closely related (~40% identity) to the kinase domains of FGF-R1, PDGF-R and c-kit. The intracellular portions of Tie2 contain all of the features of tyrosine kinases, including a GXGXXG ATP binding site consensus sequence and typical tyrosine kinase motifs (i.e., HRD-LAARN and DFGL).

These receptors have sparked interest because they are the only receptor tyrosine kinases, other than those receptors for vascular endothelial cell growth factor (VEGF), that are largely restricted to endothelial cells in their expression. There are several lines of evidence showing that Tie2 is important in angiogenesis, detailed in the following paragraphs.

a. Tie1 and Tie2 Receptor Location i. Embryological Vascular Development

The location of the Tie receptors in the embryo has been studied by a number of investigators using in situ hybridization. Korhonen et al. (*Blood* 80:2548–2555, 1992) showed that the mRNA for Tie receptors is located in endothelial cells of all forming blood vessels and in the endocardium of mouse embryos. During embryonic development, expression of the Tie receptors is seen in angioblasts and all developing vasculature. Expression of the Tie receptors follows expression of the major VEGF receptor, Flk-1, by 12–24 hours during mouse embryogenesis, perhaps suggesting sequential and different actions of these receptor systems (Schnurch and Risau, *Development* 119: 957–968, 1993). Cloning of a 1.2 Kb genomic 5' flanking region of Tie2, coupled to a lacZ gene and expressed in transgenic mice, demonstrated a selective pattern of expression in endothelial cells during embryonic development (Schlaeger et al., *Development* 121:1089–1098, 1995). Thus, the Tie2 promoter acts to assure endothelial cell-specific expression of Tie2.

ii. In Adult Tissues

The similarities between embryonic angiogenesis and pathologic angiogenesis yields the hypothesis that blocking Tie2 function, in tumors or chronic inflammatory settings, for examples, may block angiogenesis, thus blocking further cell proliferation and provide therapeutic benefit. Tie mRNA cannot be observed in adult skin, except at sites of active wound healing, where the proliferating capillaries in the granulation tissue contain abundant Tie mRNA (Korhonen et al., *Blood* 80:2548–2555, 1992). PCR amplification of cDNA from normal skin fails to show a signal for Tie receptor (Kaipainen et al., *Cancer Res.* 54:6571–6577, 1994). In contrast, a strong signal is seen with cDNA from metastasizing melanomas, where in situ studies localize this signal to the vascular endothelium. While Tie receptor expression is down-regulated in the established vasculature, it is up-regulated in the angiogenesis that occurs in the ovary during ovulation, in wounds and in tumor (breast, melanoma and renal cell carcinoma) vasculature, consistent with prevailing views that angiogenesis in the adult borrows from embryonic angiogenic mechanisms.

b. Tie Knockout Animals

Homozygous mice with a Tie2 knockout, or carrying a transgene encoding a "dominant-negative" Tie2 receptor, confirmed that the Tie2 receptor is critical for embryonic development (Dumont et al., *Genes Dev.* 8:1897–1909, 1994; Sato et al., *Nature* 376:70–74, 1995). Embryonic death in these mice occurred due to vascular insufficiency and there were dramatically reduced numbers of endothelial cells. Vasculogenesis—that is the differentiation of endothelial cells and the in situ formation of vessels—appeared relatively normal in mice lacking Tie2. The subsequent sprouting and remodeling resulting in formation of vessel branches (angiogenesis) was drastically reduced in the Tie2 mutant mice embryos. This lack of sprouting and angiogenesis resulted in substantial growth retardation, particularly of the brain, neural tube and heart, resulting in lack of viability. This exemplifies the critical importance of Tie2 in angiogenesis. This is significant, as angiogenesis is regulated by a number of growth factors. Interestingly, Flk1 (VEGF receptor) knockout mice exhibit embryo lethal defects in vasculogenesis, that occur earlier than those of Tie2 disruption. Disruption of the Tie1 receptor yields a much different, and later, defective phenotype; the mouse embryo dies late in development due to hemorrhage resulting from defective integrity of an otherwise well-formed vasculature. Taken together, these studies suggest that the VEGF/Flk1 and Tie systems operate in sequential fashion, with Tie2 having a critical role in angiogenesis.

c. Tie2 Ligands

Recently, two ligands for the Tie2 receptor have been reported. Angiopoietin-1 binds and induces the tyrosine phosphorylation of Tie2 and its expression in vivo is in close proximity with developing blood vessels (Davis et al., *Cell* 87:1161–1169, 1996). Mice engineered to lack Angiopoietin-1 display angiogenic deficits reminiscent of those previously seen in mice lacking Tie2 receptors, demonstrating that Angiopoietin-1 is a primary physiologic ligand for Tie2 and that Tie2 has critical in vivo angiogenic actions (Suri et al., *Cell* 87:1171–1180, 1996). Angiopoietin-2 was identified by homology screening and shown to be a naturally occurring antagonist for Tie2 receptors. Transgenic overexpression of Angiopoietin-2 disrupts blood vessel formation in the mouse embryo (Maisonpierre et al., *Science* 277: 55–60, 1997). Together, these results support a role for Tie2 receptors in angiogenesis.

d. Tie2 Inhibition

Based upon the importance of Tie2 receptors in angiogenesis, inhibition of Tie2 kinase activity is predicted to interrupt angiogenesis, providing disease-specific therapeutic effects. Recently, Lin et al. (*J. Clin. Invest.* 100:2072–2078, 1997) has shown that exogenously administered soluble Tie2 receptor inhibited angiogenesis and cancer growth in animal models. Thus inhibition of Tie2 receptors by other means, such as inhibition of Tie2 receptor kinase activity, is expected to have therapeutic benefit in proliferative diseases involving angiogenesis.

The current application teaches the novel finding that compounds of specific structure can inhibit the kinase activity of the Tie2 receptor, block its signal transduction and thus may be beneficial for proliferative diseases via inhibition of signals for angiogenesis.

SUMMARY OF THE INVENTION

The present invention is the finding that novel compounds can inhibit Tie2 kinase, and that these compounds can be used for inhibition of angiogenesis for the treatment of chronic inflammatory or proliferative or angiogenic diseases which are caused by excessive or inappropriate angiogenesis. The preferred compounds for use as Tie2 receptor kinase inhibitors are those compounds of Formula (I) as noted herein, including pharmaceutically acceptable salts, hydrates and solvates thereof.

DETAILED DESCRIPTION OF THE INVENTION

The present invention relates to novel compounds of formula (I) for use in the treatment of disorders associated with the inhibition of Tie2 receptor kinase inhibitors.

Accordingly, the present invention provides compounds of Formula (I) and pharmaceutically acceptable salts, solvates, and hydrates thereof (hereinafter alternatively collectively referred to as "compound(s) of Formula (I)"):

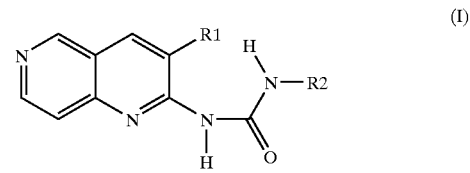

wherein:

R1 is selected from the group consisting of aryl, aralkyl, heteroaryl, heteroarylalkyl, heterocyclic, heterocyclicalkyl, aroyl, and alkanoyl;

R2 is selected from the group consisting of H, C 1–10 alkyl, cycloalkyl, aryl, aralkyl, heteroaryl, heteroarylalkyl, heterocyclic, heterocyclicalkyl, alkenyl, cycloalkenyl, and alkynyl; and wherein R1 and R2 may be independently optionally substituted.

The following terms, as used herein, refer to:

"$C_{1-10}$alkyl" or "alkyl"—both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, and n-pentyl.

"cycloalkyl" is used herein to mean carbocyclic radicals, preferably of 3 to 8 carbons, including but not limited to cyclopropyl, cyclopentyl and cyclohexyl.

"aryl"—phenyl and naphthyl.

"heteroaryl" (on its own or in any combination, such as "heteroaryloxy", or "heteroaryl alkyl")—a 5–10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, thiazole, thiadiazole, triazole, imidazole, or benzimidazole.

"heterocyclic" (on its own or in any combination, such as "heterocyclylalkyl")—a saturated or partially unsaturated 4–10 membered ring system in which one or more rings contain one or more heteroatoms selected from the group consisting of N, O, or S; such as, but not limited to, pyrrolidine, piperidine, piperazine, morpholine, tetrahydro pyran, pyran, or imidazolidine.

"aralkyl" or "heteroarylalkyl" or "heterocyclicalkyl" is used herein to mean $C_{1-4}$ alkyl as defined above attached to an aryl, heteroaryl or heterocyclic moiety as also defined herein, including benzyl and phenethyl, unless otherwise indicated.

"aroyl"—a C(O)Ar, wherein Ar is a phenyl, naphthyl, or aryl alkyl derivative such as defined above.

"alkanoyl"—a $C(O)C_{1-10}$alkyl wherein the alkyl is as defined above.

"alkenyl" is used herein at all occurrences to mean a straight or branched chain radical of 2–10 carbon atoms, unless the chain length is otherwise limited, which has at least one carbon-carbon double bond, including, but not limited to ethenyl, 1-propenyl, 2-propenyl, 2-methyl-1-propenyl, 1-butenyl, and 2-butenyl.

"cycloalkenyl" is used herein to mean a cyclic radical, preferably of 5 to 8 carbons, which has at least one carbon-carbon double bond, including but not limited to cyclopentenyl and cyclohexenyl.

"alkynyl" is used herein at all occurrences to mean a straight or branched chain radical of 2–10 carbon atoms, unless the chain length is otherwise limited, which has at least one carbon-carbon triple bond, including, but not limited to propynyl, 1-butynyl, and 2-butynyl.

"halo" or "halogen", include the halogens: chloro, fluoro, bromo and iodo.

As used herein, "optionally substituted", unless specifically defined, shall mean that a moiety is substituted with one or more groups such as:
halogen (such as fluorine, chlorine, bromine or iodine);
hydroxy;
hydroxy substituted $C_{1-10}$ alkyl;
$C_{1-10}$ alkoxy (such as methoxy or ethoxy);
$S(O)_m$ alkyl, wherein m is 0, 1 or 2 (such as methyl thio, methylsulfinyl or methyl sulfonyl);
amino;
mono-substituted amino (such as mono-$C_{1-6}$ alkyl substituted amino);
di-substituted amino (such di-$C_{1-6}$ alkyl substituted amino));
$C_{1-10}$ alkyl (such as methyl, ethyl, propyl, isopropyl, t-butyl, etc.);
cycloalkyl;
cycloalkyl alkyl (such as cyclopropyl methyl);
halosubstituted $C_{1-10}$ alkyl (such as $CF_3$);
aryl (such as phenyl) or aralkyl (such as benzyl or phenethyl), wherein the aryl moieties may also be substituted one to two times by halogen, hydroxy, hydroxy substituted alkyl, $C_{1-10}$ alkoxy, $S(O)_m$ alkyl, amino, mono-substituted amino, di-substituted amino, $C_{1-10}$ alkyl, or halosubstituted $C_{1-10}$ alkyl such as described above;
alkenyl;
alkynyl.

Where R2 is alkenyl, cycloalkenyl, or alkynyl, the unsaturated linkage, i.e., the vinylene or acetylene linkage, is preferably not directly attached to the nitrogen. Similarly, where the compound otherwise comprises an alkenyl or alkynyl substituent group, the vinyl or acetylene linkage is preferably not directly attached to a nitrogen, oxygen or sulfur which may be present in the compound.

R1 is preferably selected from substituted or unsubstituted aryl (more preferably phenyl) and heteroaryl, and is more preferably substituted phenyl. R2 is preferably selected from $C_{1-10}$ alkyl, cycloalkyl, aryl, and heterocyclic. For example, R1 is suitably substituted or unsubstituted phenyl, thiophene, pyridinyl, or pyrazole. The substituent groups of such substituted R1 are more suitably one or more, preferably 1–2, groups selected from $C_{1-10}$ alkyl (preferably methyl), halo (preferably fluoro, chloro), halosubstituted $C_{1-10}$ alkyl (preferably $CF_3$), $C_{1-10}$ alkoxy (preferably methoxy), amino, mono-substituted amino, and di-substituted amino (preferably dimethyl amino). Where R1 is a phenyl derivative, the substituents may suitably be, e.g., in the 2-, 3-, 2,5-, 2,6-, 3,4- or 3,5-ring position. Where R1 is a thiophene or pyrazole derivative, the substituents may suitably be, e.g., in the 2-ring position.

For example, R2 is suitably selected from the group consisting of $C_{1-10}$ alkyl (preferably $C_{1-4}$ alkyl), cycloalkyl, substituted aryl (preferably substituted phenyl), and heterocyclic. More suitably R2 is selected from the group consisting of methyl, ethyl, tert-butyl, cyclohexyl, substituted phenyl, and pyran. Substituted phenyl is more suitably substituted by one or more, preferably 1–2, groups selected from the group consisting of halo (preferably fluoro, chloro), and $C_{1-10}$ alkoxy (preferably methoxy). Where R2 is a phenyl derivative, the substituents may suitably be, e.g., in the 3-, 4-, or 3,4-ring position.

Particularly suitable compounds include those wherein R1 is substituted phenyl and R2 is $C_{1-10}$ alkyl, cycloalkyl, or heterocyclic, more preferably $C_{1-4}$ alkyl (e.g., t-butyl, methyl), cyclohexyl, or tetrahydropyranyl. Preferred substituents on such R1 are halo (e.g., chloro, fluoro) and $C_{1-4}$ alkyl (e.g., methyl), such as 2,6-dichloro, 2-chloro-6-fluoro, and 2,5-dimethyl.

Preferred are the compounds:
3-[2,6-dichlorophenyl]-1,6-naphthyridin-2'-2-[N'-(1,1-dimethylethyl)-urea];
1-tert-butyl-3-[3-(2-chloro-6-fluoro-phenyl)-[1,6]naphthyridin-2-yl]-urea;
1-[3-(2-chloro-6-fluoro-phenyl)-[1,6]naphthyridin-2-yl]-3-(tetrahydro-pyran-2-yl)
1-tert-butyl-3-[3-(2,5-dimethyl-phenyl)-[1,6]naphthyridin-2-yl]-urea;
1-[3-(2,5-dimethyl-phenyl)-[1,6]naphthyridin-2-yl]-3-ethyl-urea; and
1-[3-(2,5-dimethyl-phenyl)-[1,6]naphthyridin-2-yl]-3-(tetrahydro-pyran-2-yl)-urea.

Suitable pharmaceutically acceptable salts are well known to those skilled in the art and include basic salts of inorganic and organic acids, such as hydrochloric acid, hydrobromic acid, sulfuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of Formula (I) may also be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations.

It is recognized that the compounds of the present invention may exist as stereoisomers, regioisomers or diastereoisomers. These compounds may contain one or more asymmetric carbon atoms and may exist in racemic and optically active forms. All of these compounds are included within the scope of the present invention.

SYNTHETIC METHODS

The following describes how compounds of the present invention may be prepared from readily available starting materials.

Scheme 1:

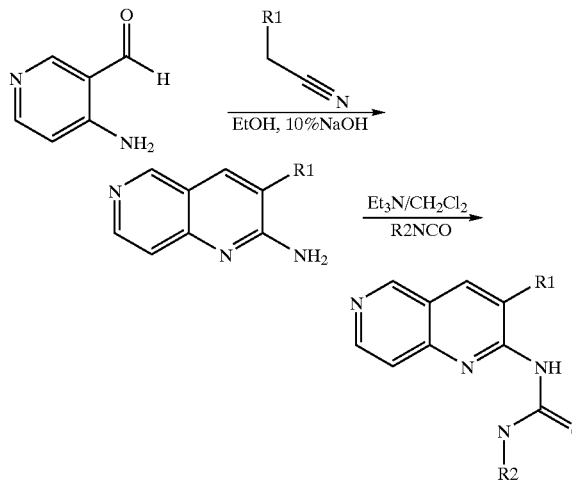

Condensation of 4-aminonicotinaldehyde (Turner, J. A. *J. Org. Chem.* 1983,48, 3401) with substituted acetonitriles by the literature procedure (Hawes, E. M.; Gorecki, D. K. J. *J. Heterocycl. Chem.* 1972, 9(3), 703) affords 2-amino-3-substituted 1,6-naphthyridines. Reaction of the 2-amino-3-substituted 1,6-naphthyridine intermediate with a substituted isocyanate under standard conditions affords the 2-urea-3-substituted 1,6-naphthyridine.

Pharmaceutically acceptable acid addition salts of compounds of Formula (I) may be obtained in known manner, for example by treatment thereof with an appropriate amount of acid in the presence of a suitable solvent.

The compounds of the present invention may be used in the treatment or prophylaxis of disease states exacerbated or characterized by excessive or otherwise inappropriate or undesirable angiogenesis. The term "excessive or otherwise inappropriate or undesirable angiogenesis" as used herein includes, but is not limited to, diseases which are characterized by hemangiomas and ocular diseases, diseases which are characterized by vessel (vasculature) proliferation with accompanying tissue proliferation, such as occurs in cancer, metastasis, arthritis, psoriasis and atherosclerosis, ocular neovascularizations, such as diabetic retinopathy and macular degeneration, tumor growth and metastasis, atherosclerosis, and certain arthritic conditions. Tie2 tyrosine kinase receptor inhibitors of the present invention will be of utility in the blocking of the angiogenic component of these disease states.

In order to use a compound of the present invention in therapy, it will normally be formulated into a pharmaceutical composition in accordance with standard pharmaceutical practice. This invention, therefore, also relates to a pharmaceutical composition comprising an effective, non-toxic amount of a compound of Formula (I), and a pharmaceutically acceptable carrier or diluent.

Compounds of Formula (I), and pharmaceutical compositions incorporating such compounds may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will typically be in the form of a syrup, emulsion, soft gelatin capsule, sterile injectable liquid such as an ampule or nonaqueous liquid suspension.

Compounds of Formula (I) may be administered non-systemically (i.e., the compound does not significantly enter the blood stream), such as topically. This includes the application of a compound of Formula (I) externally to the epidermis or the buccal cavity and the instillation of such a compound into the ear, eye and nose, such that the compound does not significantly enter the blood stream.

Formulations suitable for topical administration include liquid or semi-liquid preparations suitable for penetration through the skin to the site of disease/inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. While it may comprise as much as 10% w/w, it will preferably comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as stearic or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably include a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of formula (I) may be administered systemically, e.g. orally or parenterally (that is by intravenous, intramuscular, subcutaneous, intranasal, intrarectal, intravaginal or intraperitoneal administration). The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol formulation or a metered dose inhaler, may be prepared by conventional techniques. Appropriate dosage forms for other oral administration may be prepared by conventional techniques.

The compounds of Formula (I) are administered in an amount sufficient to inhibit Tie2 receptor activity such that it is regulated down to normal levels, or in some cases to subnormal levels, so as to ameliorate or prevent the disease state.

For all methods of use disclosed herein for the compounds of Formula (I), the daily oral dosage regimen will preferably be from about 0.1 to about 80 mg/kg of total body weight, preferably from about 0.2 to 30 mg/kg, more preferably from about 0.5 mg to 15 mg. The daily parenteral dosage regimen will be from about 0.1 to about 80 mg/kg of total body weight, preferably from about 0.2 to about 30 mg/kg, and more preferably from about 0.5 mg to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) given per day for a defined number of days, can be ascertained by those skilled in the art using conventional course of treatment determination tests.

No toxicological effects are expected when a compound of the invention is administered in the above mentioned dosage range.

SYNTHETIC EXAMPLES

The invention will now be described by reference to the following examples which are merely illustrative and are not to be construed as a limitation of the scope of the present invention.

All temperatures are given in degrees centigrade (° C.), all solvents are highest available purity and all reactions run under anhydrous conditions in an argon atmosphere unless otherwise indicated. Mass spectra were performed upon a VG Zab mass spectrometer using fast atom bombardment or on a micromass platform electrospray ionization mass spectrometer in the positive ion mode using 95:5 $CH_3CN$/$CH_3OH$ with 1% formic acid as the carrier solvent, unless otherwise indicated. $^1$H-NMR (hereinafter "NMR") spectra were recorded at 250 MHz using a Bruker AM 250 or Am 400 spectrometer. Multiplicities indicated are: s=singlet, d=doublet, t=triplet, q=quartet, m=multiplet and br indicates a broad signal. Sat. indicates a saturated solution, eq indicates the proportion of a molar equivalent of reagent relative to the principal reactant. Flash chromatography is run over Merck Silica gel 60 (230–400 mesh).

Example 1

Preparation of 3-[2,6-Dichlorophenyl]-1,6-naphthyridin-2'-2-[N'-(1,1-dimethylethyl)-urea]

a) 4-Aminonicotinaldehyde

In this and other examples, is prepared by the method described by Turner, J. A., *J. Org. Chem.* 1983,48, 3401.

b) 3-[2,6-Dichlorophenyl]-1,6-naphthyridin-2-amine.

4-Aminonicotinaldehyde (100 mg, 0.78 millimole (hereinafter "mmol")), 2,6-dichlorophenylacetonitrile (217 mg, 1.2 mmol), 10% aqueous NaOH (0.101 mL, 0.25 mmol) and 700 uL of absolute ethanol are combined and heated at 65° C. for 24 hours (hereinafter "h"). The reaction mixture is cooled to ambient temperature and the solvents are evaporated under reduced pressure. The residue is diluted with 700 uL of DMSO filtered and purified with preparative reverse phase chromatography to afford the title compound as a yellow solid (191 mg, 84% yield). MS ES$^+$ m/z=290.

c) 3-[2,6-Dichlorophenyl]-1,6-naphthyridin-2'-2-[N'-(1,1-dimethylethyl)-urea].

3-[2,6-dichlorophenyl]-1,6-naphthyridin-2-amine (51 mg, 0.176 mmol) and t-butyl isocyanate (17 mg, 0.176 mmol) is dissolved in $CH_2Cl_2$ (1 mL). NaH [60% dispersion in mineral oil (7 mg, 0.176 mmol)] is added and stirred for 24 h. The reaction is filtered and washed with DMF (1 mL). The residue is concentrated and purified by chromatography on silical gel eluting with 25:1 in $CH_2Cl_2$:MeOH to afford the title compound as a white solid (25 mg, 36% yield). MS ES$^+$ m/z=390. $^1$H NMR (CDCl$_3$): 9.32 (s, 1H), 8.72 (m, 1H), 8.40 (m, 1H), 7.95 (m, 1H), 7.55 (m, 3H), 1.50 (s, 9H).

Examples 2–79 are prepared as in Example 1, except that the nitrile and/or isocyanate are varied in procedures (b) and/or (c) as indicated below.

Ex. 2

1-tert-Butyl-3-[3-(3,5-dimethyl-phenyl)-[1,6]naphthyridin-2-yl]-urea

Procedure same as Example 1 b and c except use 3,5-dimethylphenylacetonitrile in procedure b. LC/MS ES$^+$ m/z=349 (M+H).

Ex. 3

1-tert-Butyl-3-(3-thiophen-3-yl-[1,6]naphthyridin-2-yl)-urea

Procedure same as Example 1 b and c except use 3-thiopheneacetonitrile in procedure b. LC/MS ES$^+$ m/z=327 (M+H).

Ex. 4

1-tert-Butyl-3-[3-(2-chloro-6-fluoro-phenyl)-[1,6]naphthyridin-2-yl]-urea

Procedure same as Example 1 b and c except use 2-chloro-6-fluoro-phenylacetonitrile in procedure b. LC/MS ES$^+$ m/z=373 (M+H).

Ex. 5

1-tert-Butyl-3-[3-(2,5-dimethyl-phenyl)-[1,6]naphthyridin-2-yl]-urea

Procedure same as Example 1 b and c except use 2,5-dimethyphenylacetonitrile in procedure b. LC/MS ES$^+$ m/z=349 (M+H).

Ex. 6

1-tert-Butyl-3-(3-pyridin-2-yl-[1,6]naphthyridin-2-yl)-urea

Procedure same as Example 1 b and c except use 3-pyridylacetonitrile in procedure b. LC/MS ES$^+$ m/z=322 (M+H).

Ex. 7

1-tert-Butyl-3-[3-(2-methoxy-phenyl)-[1,6]naphthyridin-2-yl]-urea

Procedure same as Example 1 b and c except use 2-methoxyphenylacetonitrile in procedure b. LC/MS ES$^+$ m/z=351 (M+H).

Ex. 8

1-tert-Butyl-3-[3-(3,4-difluoro-phenyl)-[1,6]naphthyridin-2-yl]-urea

Procedure same as Example 1 b and c except use 3,4-difluorophenylacetonitrile in procedure b. LC/MS ES$^+$ m/z=357 (M+H).

Ex. 9

1-[3-(5-Acetyl-thiophen-2-yl)-[1,6]naphthyridin-2-yl]-3-tert-butyl-urea

Procedure same as Example 1 b and c except use 5-acetyl-thiopheneacetonitrile in procedure b. LC/MS ES$^+$ m/z=369 (M+H).

Ex. 10

1-tert-Butyl-3-(3-m-tolyl-[1,6]naphthyridin-2-yl)-urea

Procedure same as Example 1 b and c except use 3-methylphenylacetonitrile in procedure b. LC/MS ES$^+$ m/z=335 (M+H).

Ex. 11

1-Cyclohexyl-3-[3-(3,5-dimethyl-phenyl)-[1,6]naphthyridin-2-yl]-urea

Procedure same as Example 1 b and c except use 3,5-dimethylphenylacetonitrile in procedure b and cyclohexyl isocyanate in procedure c. LC/MS ES$^+$ m/z=375 (M+H).

Ex. 12

1-Cyclohexyl-3-[3-(5-dimethylamino-[1,3,4]oxadiazol-2-yl)-[1,6]naphthyridin-2-yl]-urea Procedure same as Example 1 b and c except use 3-(5-dimethylamino-[1,3,4]oxadiazole)-acetonitrile in procedure b and cyclohexyl isocyanate in procedure c. LC/MS ES$^+$ m/z=382 (M+H).

Ex. 13

1-Cyclohexyl-3-(3-thiophen-3-yl-[1,6]naphthyridin-2-yl)-urea

Procedure same as Example 1 b and c except use 3-thiopheneacetonitrile in procedure b and cyclohexyl isocyanate in procedure c. LC/MS ES$^+$ m/z=353 (M+H).

Ex. 14

1-[3-(2-Chloro-6-fluoro-phenyl)-[1,6]naphthyridin-2-yl]-3-cyclohexyl-urea

Procedure same as Example 1 b and c except use 2-chloro-6-fluoro-phenylacetonitrile in procedure b and cyclohexyl isocyanate in procedure c. LC/MS ES$^+$ m/z=399 (M+H).

Ex. 15

1-Cyclohexyl-3-[3-(2,5-dimethyl-phenyl)-[1,6]naphthyridin-2-yl]-urea

Procedure same as Example 1 b and c except use 2,5-dimethyphenylacetonitrile in procedure b and cyclohexyl isocyanate in procedure c. LC/MS ES$^+$ m/z=375 (M+H).

Ex. 16

1-Cyclohexyl-3-[3-(2-methoxy-phenyl)-[1,6]naphthyridin-2-yl]-urea

Procedure same as Example 1 b and c except use 2-methoxyphenylacetonitrile in procedure b and cyclohexyl isocyanate in procedure c. LC/MS ES$^+$ m/z=377 (M+H).

Ex. 17

1-Cyclohexyl-3-[3-(3,4-difluoro-phenyl)-[1,6]naph-thyridin-2-yl]-urea

Procedure same as Example 1 b and c except use 3,4-difluorophenylacetonitrile in procedure b and cyclohexyl isocyanate in procedure c. LC/MS ES$^+$ m/z=399 (M+H).

Ex. 18

1-[3-(5-Acetyl-thiophen-2-yl)-[1,6]naphthyridin-2-yl]-3-cyclohexyl-urea

Procedure same as Example 1 b and c except use 5-acetyl-thiopheneacetonitrile in procedure b and cyclohexyl isocyanate in procedure c. LC/MS ES$^+$ m/z=395 (M+H).

Ex. 19

1-Cyclohexyl-3-(3-m-tolyl-[1,6]naphthyridin-2-yl)-urea

Procedure same as Example 1 b and c except use 3-methylphenylacetonitrile in procedure b and cyclohexyl isocyanate in procedure c. LC/MS ES$^+$ m/z=361 (M+H).

Ex. 20

1-(3-Acetyl-phenyl)-3-[3-(5-dimethylamino-[1,3,4]oxadiazol-2-yl)-[1.6]naphthyridin-2-yl]-urea Procedure same as Example 1 b and c except use 3-(5-dimethylamino-[1,3,4]oxadiazole)-acetonitrile in procedure b and 3-acetyl-phenyl isocyanate in procedure c. LC/MS ES$^+$ m/z=418 (M+H).

Ex. 21

1-(3-Acetyl-phenyl)-3-(3-thiophen-3-yl-[1,6]naph-thyridin-2-yl)-urea

Procedure same as Example 1 b and c except use 3-thiopheneacetonitrile in procedure b and 3-acetyl-phenyl isocyanate in procedure c. LC/MS ES$^+$ m/z=389 (M+H).

Ex. 22

1-(3-Acetyl-phenyl)-3-[3-(3,5-bis-trifluoromethyl-phenyl)-[1,6]naphthyridin-2-yl]-urea Procedure same as Example 1 b and c except use 3,5-bis-trifluoromethyl-phenylacetonitrile in procedure b and 3-acetyl-phenyl isocyanate in procedure c. LC/MS ES$^+$ m/z=519 (M+H).

Ex. 23

1-(3-Acetyl-phenyl)-3-[3-(2-chloro-6-fluoro-phenyl)-[1,6]naphthyridin-2-yl]-urea Procedure same as Example 1 b and c except use 2-chloro-6-fluoro-phenylacetonitrile in procedure b and 3-acetyl-phenyl isocyanate in procedure c. LC/MS ES$^+$ m/z=435 (M+H).

Ex. 24

1-(3-Acetyl-phenyl)-3-[3-(2,5-dimethyl-phenyl)-[1,6]naphthyridin-2-yl]-urea

Procedure same as Example 1 b and c except use 2,5-dimethyphenylacetonitrile in procedure b and 3-acetyl-phenyl isocyanate in procedure c. LC/MS ES$^+$ m/z=411 (M+H).

Ex. 25

1-(3-Acetyl-phenyl)-3-(3-pyridin-2-yl-[1,6]naphthy-ridin-2-yl)-urea

Procedure same as Example 1 b and c except use 3-pyridylacetonitrile in procedure b and 3-acetyl-phenyl isocyanate in procedure c. LC/MS ES$^+$ m/z=384 (M+H).

Ex. 26

1-(3-Acetyl-phenyl)-3-[3-(2-methoxy-phenyl)-[1,6]naphthyridin-2-yl]-urea

Procedure same as Example 1 b and c except use 3-methylphenylacetonitrile in procedure b and 3-acetyl-phenyl isocyanate in procedure c. LC/MS ES$^+$ m/z=413 (M+H).

Ex. 27

1-(3-Acetyl-phenyl)-3-[3-(3,4-difluoro-phenyl)-[1,6]naphthyridin-2-yl]-urea

Procedure same as Example 1 b and c except use 3,4-difluorophenylacetonitrile in procedure b and 3-acetyl-phenyl isocyanate in procedure c. LC/MS ES$^+$ m/z=419 (M+H).

Ex. 28

1-(3-Acetyl-phenyl)-3-[3-(5-acetyl-thiophen-2-yl)-[1,6]naphthyridin-2-yl]-urea

Procedure same as Example 1 b and c except use 5-acetyl-thiopheneacetonitrile in procedure b and 3-acetyl-phenyl isocyanate in procedure c. LC/MS ES$^+$ m/z=431 (M+H).

Ex. 29

1-(3-Acetyl-phenyl)-3-(3-m-tolyl-[1,6]naphthyridin-2-yl)-urea

Procedure same as Example 1 b and c except use 5-acetyl-thiopheneacetonitrile in procedure b and 3-acetyl-phenyl isocyanate in procedure c. LC/MS ES$^+$ m/z=397 (M+H).

Ex. 30

1-(3-Chloro-4-fluoro-phenyl)-3-[3-(3,5-dimethyl-phenyl)-[1,6]naphthyridin-2-yl]-urea Procedure same as Example 1 b and c except use 3,5-dimethylphenylacetonitrile in procedure b and 3-chloro-4-fluoro-phenyl isocyanate in procedure c. LC/MS ES$^+$ m/z=421 (M+H).

Ex. 31

1-(3-Chloro-4-fluoro-phenyl)-3-[3-(5-dimethylamino-[1,3,4]oxadiazol-2-yl)-[1,6]naphthyridin-2-yl]-urea Procedure same as Example 1 b and c except use 3-(5-dimethylamino-[1,3,4]oxadiazole)-acetonitrile in procedure b and 3-chloro-4-fluoro-phenyl isocyanate in procedure c. LC/MS ES$^+$ m/z=428 (M+H).

Ex. 32

1-(3-Chloro-4-fluoro-phenyl)-3-(3-thiophen-3-yl-[1,6]naphthyridin-2-yl)-urea

Procedure same as Example 1 b and c except use 3-thiopheneacetonitrile in procedure b and 3-chloro-4-fluoro-phenyl isocyanate in procedure c. LC/MS ES$^+$ m/z=399 (M+H).

Ex. 33

1-[3-(Bis-trifluoromethyl-phenyl)-[1,6]naphthyridin-2-yl]-3-(chloro-fluoro-phenyl)-urea Procedure same as Example 1 b and c except use 3,5-bis-trifluoromethyl-phenylacetonitrile in procedure b and 3-chloro-4-fluoro-phenyl isocyanate in procedure c. LC/MS ES$^+$ m/z=529 (M+H).

Ex. 34

1-(3-Chloro-4-fluoro-phenyl)-3-[3-(2-chloro-6-fluoro-phenyl)-[1,6]naphthyridin-2-yl]-urea Procedure same as Example 1 b and c except use 2-chloro-6-fluoro-phenylacetonitrile in procedure b and 3-chloro-4-fluoro-phenyl isocyanate in procedure c. LC/MS ES$^+$ m/z=445 (M+H).

Ex. 35

1-(3-Chloro-4-fluoro-phenyl)-3-[3-(2,5-dimethyl-phenyl)-[1,6]naphthyridin-2-yl]-urea Procedure same as Example 1 b and c except use 2,5-dimethyphenylacetonitrile in procedure b and 3-chloro-4-fluoro-phenyl isocyanate in procedure c. LC/MS ES$^+$ m/z=421 (M+H).

Ex. 36

1-(3-Chloro-4-fluoro-phenyl)-3-[3-(2-methoxy-phenyl)-[1,6]naphthyridin-2-yl]-urea Procedure same as Example 1 b and c except use 2-methoxyphenylacetonitrile in procedure b and 3-chloro-4-fluoro-phenyl isocyanate in procedure c. LC/MS ES$^+$ m/z=423 (M+H).

Ex. 37

1-(3-Chloro-4-fluoro-phenyl)-3-[3-(3,4-difluoro-phenyl)-[1,6]naphthyridin-2-yl]-urea Procedure same as Example 1 b and c except use 3,4-difluorophenylacetonitrile in procedure b and 3-chloro-4-fluoro-phenyl isocyanate in procedure c. LC/MS ES$^+$ m/z=429 (M+H).

Ex. 38

1-[3-(5-Acetyl-thiophen-2-yl)-[1,6]naphthyridin-2-yl]-3-(3-chloro-4-fluoro-phenyl)-urea Procedure same as Example 1 b and c except use 5-acetyl-thiopheneacetonitrile in procedure b and 3-chloro-4-fluoro-phenyl isocyanate in procedure c. LC/MS ES$^+$ m/z=441 (M+H).

Ex. 39

1-(3-Chloro-4-fluoro-phenyl)-3-(3-m-tolyl-[1,6]naphthyridin-2-yl)-urea

Procedure same as Example 1 b and c except use 3-methylphenyleacetonitrile in procedure b and 3-chloro-4-fluoro-phenyl isocyanate in procedure c. LC/MS ES$^+$ m/z=407 (M+H).

Ex. 40

1-[3-(3,5-Dimethyl-phenyl)-[1,6]naphthyridin-2-yl]-3-(tetrahydro-pyran-2-yl)-urea Procedure same as Example 1 b and c except use 3,5-dimethylphenylacetonitrile in procedure b and tetrahydro-pyran-2-isocyanate in procedure c. LC/MS ES$^+$ m/z=377 (M+H).

Ex. 41

1-[3-(5-Dimethylamino-[1,3,4]oxadiazol-2-yl)-[1,6]naphthyridin-2-yl]-3-(tetrahydro-pyran-2-yl)-urea Procedure same as Example 1 b and c except use 3-(5-dimethylamino-[1,3,4]oxadiazole)-acetonitrile in procedure b and tetrahydro-pyran-2-isocyanate in procedure c. LC/MS ES$^+$ m/z=384 (M+H).

Ex. 42

1-(Tetrahydro-pyran-2-yl)-3-(3-thiophen-3-yl-[1,6]naphthyridin-2-yl)-urea

Procedure same as Example 1 b and c except use 3-thiopheneacetonitrile in procedure b and tetrahydro-pyran-2-isocyanate in procedure c. LC/MS ES$^+$ m/z=355 (M+H).

Ex. 43

1-[3-(Bis-trifluoromethyl-phenyl)-[1,6]naphthyridin-2-yl]-3-(tetrahydro-pyran-2-yl)-urea Procedure same as Example 1 b and c except use 3,5-bis-trifluoromethyl-phenylacetonitrile in procedure b and tetrahydro-pyran-2-isocyanate in procedure c. LC/MS ES$^+$ m/z=385 (M+H).

Ex. 44

1-[3-(2-Chloro-6-fluoro-phenyl)-[1,6]naphthyridin-2-yl]-3-(tetrahydro-pyran-2-yl)-urea Procedure same as Example 1 b and c except use 2-chloro-6-fluoro-phenylacetonitrile in procedure b and tetrahydro-pyran-2-isocyanate in procedure c. LC/MS ES$^+$ m/z=401 (M+H).

Ex. 45

1-[3-(2,5-Dimethyl-phenyl)-[1,6]naphthyridin-2-yl]-3-(tetrahydro-pyran-2-yl)-urea Procedure same as Example 1 b and c except use 2,5-dimethyphenylacetonitrile in procedure b and tetrahydro-pyran-2-isocyanate in procedure c. LC/MS ES$^+$ m/z=377 (M+H).

Ex. 46

1-(3-Pyridin-2-yl-[1,6]naphthyridin-2-yl)-3-(tetrahydro-pyran-2-yl)-urea

Procedure same as Example 1 b and c except use 3-pyridylacetonitrile in procedure b and tetrahydro-pyran-2-isocyanate in procedure c. LC/MS ES$^+$ m/z=350 (M+H).

Ex. 47

1-[3-(2-Methoxy-phenyl)-[1,6]naphthyridin-2-yl]-3-(tetrahydro-pyran-2-yl)-urea

Procedure same as Example 1 b and c except use 2-methoxyphenylacetonitrile in procedure b and tetrahydro-pyran-2-isocyanate in procedure c. LC/MS ES$^+$ m/z=379 (M+H).

Ex. 48

1-[3-(3,4-Difluoro-phenyl)-[1,6]naphthyridin-2-yl]-3-(tetrahydro-pyran-2-yl)-urea Procedure same as Example 1 b and c except use 3,4-difluorophenylacetonitrile in procedure b and tetrahydro-pyran-2-isocyanate in procedure c. LC/MS ES$^+$ m/z=385 (M+H).

Ex. 49

1-(Tetrahydro-pyran-2-yl)-3-(3-m-tolyl-[1,6]naphthyridin-2-yl)-urea

Procedure same as Example 1 b and c except use 3-methylphenyleacetonitrile in procedure b and tetrahydro-pyran-2-isocyanate in procedure c. LC/MS ES$^+$ m/z=363 (M+H).

Ex. 50

1-[3-(3,5-Dimethyl-phenyl)-[1,6]naphthyridin-2-yl]-3-ethyl-urea

Procedure same as Example 1 b and c except use 3,5-dimethylphenylacetonitrile in procedure b and ethyl isocyanate in procedure c. LC/MS ES$^+$ m/z=321 (M+H).

Ex. 51

1-Ethyl-3-(3-thiophen-3-yl-[1,6]naphthyridin-2-yl)-urea

Procedure same as Example 1 b and c except use 3-thiopheneacetonitrile in procedure b and ethyl isocyanate in procedure c. LC/MS ES$^+$ m/z=299 (M+H).

Ex. 52

1-[3-(Bis-trifluoromethyl-phenyl)-[1,6]naphthyridin-2-yl]-3-ethyl-urea

Procedure same as Example 1 b and c except use 3,5-bis-trifluoromethyl-phenylacetonitrile in procedure b and ethyl isocyanate in procedure c. LC/MS ES$^+$ m/z=429 (M+H).

Ex. 53

1-[3-(2-Chloro-6-fluoro-phenyl)-[1,6]naphthyridin-2-yl]-3-ethyl-urea

Procedure same as Example 1 b and c except use 2-chloro-6-fluoro-phenylacetonitrile in procedure b and ethyl isocyanate in procedure c. LC/MS ES$^+$ m/z=345 (M+H).

Ex. 54

1-[3-(2,5-Dimethyl-phenyl)-[1,6]naphthyridin-2-yl]-3-ethyl-urea

Procedure same as Example 1 b and c except use 2,5-dimethyphenylacetonitrile in procedure b and ethyl isocyanate in procedure c. LC/MS ES$^+$ m/z=321 (M+H).

Ex. 55

1-Ethyl-3-(3-pyridin-2-yl-[1,6]naphthyridin-2-yl)-urea

Procedure same as Example 1 b and c except use 3-pyridylacetonitrile in procedure b and ethyl isocyanate in procedure c. LC/MS ES$^+$ m/z=294 (+H).

Ex. 56

1-Ethyl-3-[3-(2-methoxy-phenyl)-[1,6]naphthyridin-2-yl]-urea

Procedure same as Example 1 b and c except use 2-methoxyphenylacetonitrile in procedure b and ethyl isocyanate in procedure c. LC/MS ES$^+$ m/z=323 (M+H).

Ex. 57

1-[3-(3,4-Difluoro-phenyl)-[1,6]naphthyridin-2-yl]-3-ethyl-urea

Procedure same as Example 1 b and c except use 3,4-difluorophenylacetonitrile in procedure b and ethyl isocyanate in procedure c. LC/MS ES$^+$ m/z=329 (M+H).

Ex. 58

1-[3-(5-Acetyl-thiophen-2-yl)-[1,6]naphthyridin-2-yl]-3-ethyl-urea

Procedure same as Example 1 b and c except use 5-acetyl-thiopheneacetonitrile in procedure b and ethyl isocyanate in procedure c. LC/MS ES$^+$ m/z=341 (M+H).

Ex. 59

1-Ethyl-3-(3-m-tolyl-[1,6]naphthyridin-2-yl)-urea

Procedure same as Example 1 b and c except use 3-methylphenyleacetonitrile in procedure b and ethyl isocyanate in procedure c. LC/MS ES$^+$ m/z=307 (M+H).

Ex. 60

1-[3-(3,5-Dimethyl-phenyl)-[1,6]naphthyridin-2-yl]-3-(4-fluoro-phenyl)-urea

Procedure same as Example 1 b and c except use 3,5-dimethylphenylacetonitrile in procedure b and 4-fluoro-phenyl isocyanate in procedure c. LC/MS ES$^+$ m/z=387 (M+H).

Ex. 61

1-[3-(5-Dimethylamino-[1,3,4]oxadiazol-2-yl)-[1,6]naphthyridin-2-yl]-3-(4-fluoro-phenyl)-urea Procedure same as Example 1 b and c except use 3-(5-dimethylamino-[1,3,4]oxadiazole)-acetonitrile in procedure b and 4-fluoro-phenyl isocyanate in procedure c. LC/MS ES$^+$ m/z=394 (M+H).

Ex. 62

1-(4-Fluoro-phenyl)-3-(3-thiophen-3-yl-[1,6]naphthyridin-2-yl)-urea

Procedure same as Example 1 b and c except use 3-thiopheneacetonitrile in procedure b and 4-fluoro-phenyl isocyanate in procedure c. LC/MS ES$^+$ m/z=365 M+H).

Ex. 63

1-[3-(2-Chloro-6-fluoro-phenyl)-[1,6]naphthyridin-2-yl]-3-(4-fluoro-phenyl)-urea Procedure same as Example 1 b and c except use 2-chloro-6-fluoro-phenylacetonitrile in procedure b and 4-fluoro-phenyl isocyanate in procedure c. LC/MS ES$^+$ m/z=411 (M+H).

Ex. 64

1-[3-(2,5-Dimethyl-phenyl)-[1,6]naphthyridin-2-yl]-3-(4-fluoro-phenyl)-urea

Procedure same as Example 1 b and c except use 2,5-dimethyphenylacetonitrile in procedure b and 4-fluoro-phenyl isocyanate in procedure c. LC/MS ES$^+$ m/z=387 (M+H).

Ex. 65

1-(4-Fluoro-phenyl)-3-(3-pyridin-2-yl-[1,6]naphthyridin-2-yl)-urea

Procedure same as Example 1 b and c except use 3-pyridylacetonitrile in procedure b and 4-fluoro-phenyl isocyanate in procedure c. LC/MS ES$^+$ m/z=360 (M+H).

Ex. 66

1-(4-Fluoro-phenyl)-3-[3-(2-methoxy-phenyl)-[1,6]naphthyridin-2-yl]-urea

Procedure same as Example 1 b and c except use 2-methoxyphenylacetonitrile in procedure b and 4-fluoro-phenyl isocyanate in procedure c. LC/MS ES$^+$ m/z=389 (M+H).

Ex. 67

1-[3-(3,4-Difluoro-phenyl)-[1,6]naphthyridin-2-yl]-3-(4-fluoro-phenyl)-urea

Procedure same as Example 1 b and c except use 3,4-difluorophenylacetonitrile in procedure b and 4-fluoro-phenyl isocyanate in procedure c. LC/MS ES$^+$ m/z=395 (M+H).

Ex. 68

1-[3-(5-Acetyl-thiophen-2-yl)-[1,6]naphthyridin-2-yl]-3-(4-fluoro-phenyl)-urea

Procedure same as Example 1 b and c except use 5-acetyl-thiopheneacetonitrile in procedure b and 4-fluoro-phenyl isocyanate in procedure c. LC/MS ES$^+$ m/z=407 (M+H).

Ex. 69

1-(4-Fluoro-phenyl)-3-(3-m-tolyl-[1,6]naphthyridin-2-yl)-urea

Procedure same as Example 1 b and c except use 3-methylphenyleacetonitrile in procedure b and 4-fluoro-phenyl isocyanate in procedure c. LC/MS ES$^+$ m/z=373 (M+H).

Ex. 70

1-[3-(3,5-Dimethyl-phenyl)-[1,6]naphthyridin-2-yl]-3-methyl-urea

Procedure same as Example 1 b and c except use 3,5-dimethylphenylacetonitrile in procedure b and methyl isocyanate in procedure c. LC/MS ES$^+$ m/z=307 (M+H).

Ex. 71

1-Methyl-3-(3-thiophen-3-yl-[1,6]naphthyridin-2-yl)-urea

Procedure same as Example 1 b and c except use 3-thiopheneacetonitrile in procedure b and methyl isocyanate in procedure c. LC/MS ES$^+$ m/z=285 (M+H).

Ex. 72

1-[3-(Bis-trifluoromethyl-phenyl)-[1,6]naphthyridin-2-yl]-3-methyl-urea

Procedure same as Example 1 b and c except use 3,5-bis-trifluoromethyl-phenylacetonitrile in procedure b and methyl isocyanate in procedure c. LC/MS ES$^+$ m/z=415 (M+H).

Ex. 73

1-[3-(2-Chloro-6-fluoro-phenyl)-[1,6]naphthyridin-2-yl]-3-methyl-urea

Procedure same as Example 1 b and c except use 2-chloro-6-fluoro-phenylacetonitrile in procedure b and methyl isocyanate in procedure c. LC/MS ES$^+$ m/z=331 (M+H).

Ex. 74

1-[3-(2.5-Dimethyl-phenyl)-[1,6]naphthyridin-2-yl]-3-methyl-urea

Procedure same as Example 1 b and c except use 2,5-dimethyphenylacetonitrile in procedure b and methyl isocyanate in procedure c. LC/MS ES$^+$ m/z=307 (M+H).

Ex. 75

1-[3-(2-Methoxy-phenyl)-[1,6]naphthyridin-2-yl]-3-methyl-urea

Procedure same as Example 1 b and c except use 2-methoxyphenylacetonitrile in procedure b and methyl isocyanate in procedure c. LC/MS ES$^+$ m/z=309 (M+H).

Ex. 76

1-[3-(3,4-Difluoro-phenyl)-[1,6]naphthyridin-2-yl]-3-methyl-urea

Procedure same as Example 1 b and c except use 3,4-difluorophenylacetonitrile in procedure b and methyl isocyanate in procedure c. LC/MS ES$^+$ m/z=315 (M+H).

Ex. 77

1-[3-(5-Acetyl-thiophen-2-yl)-[1,6]naphthyridin-2-yl]-3-methyl-urea

Procedure same as Example 1 b and c except use 5-acetyl-thiopheneacetonitrile in procedure b and methyl isocyanate in procedure c. LC/MS ES$^+$ m/z=327 (M+H).

Ex. 78

1-Methyl-3-(3-m-tolyl-[1,6]naphthyridin-2-yl)-urea

Procedure same as Example 1 b and c except use 5-acetyl-thiopheneacetonitrile in procedure b and methyl isocyanate in procedure c. LC/MS ES$^+$ m/z=293 (M+H).

PHARMACOLOGICAL TEST METHODS

A. Measurement of Tie2 Kinase Activity

A partial cDNA clone for the Tie2 receptor is used to make protein for Tie kinase studies. In order to generate the primary screening assay, a baculovirus expressed GST fusion for Tie2 kinase domain is constructed and expressed using the commercial vector pAcG1 (Pharmingen).

This final construct is transfected into Baculovirus and soluble GST fusion products used in the screening assay. Prior work demonstrates the use of a baculovirus expressed GST fusion for the murine Tie2 kinase domain to screen for candidate target/signaling molecules (Huang et al., Oncogene 11:2097–2103, 1995).

Tie2 Kinase Activity Assay:

The Tie2 kinase activity assay is typically run in one of two ways, described as follows. Minor variations in the assay give similar results.

1. Autophosphorylation Flashplate Assay

Materials:
  Kinase buffer (final 20 mM Tris-HCl, pH7.0, 100 mM NaCl, 12 mM MgCl$_2$, 1 mM DTT)
  Gamma $^{33}$p-ATP (usually final amount of 0.5–1 uCi/well)
  ATP (final 30 uM, or other desired concentration)
  Flashplate (96-well, polystyrene microplate with plastic scintillator coated wells)
  TopCount (microplate scintillation counter)

Procedures:
  Turn on an incubator shaker and adjust temperature to 30° C.
  Add 20 ul of 3× kinase buffer per well to the Flashplate.
  Add 20 ul of protein per well except for background.
  Add test compounds, typically 1–2 ul in DMSO stocks.
  Add 20 ul of a mixture of gamma $^{33}$p-ATP and cold ATP (typically 1:1 v/v) per well.
  Total volume is 60 ul.
  Cover with transparent polyester film.
  Incubate at 30° C. for two hours in shaker, or desired time.
  Take Flashplate out of the shaker, wash five times (for example, with 300 ul of 10 uM ATP in 1×PBS per well).
  Read plate on TopCount or other counting instrument. Results are calculated as % inhibition and IC50, using normal calculation methods.

2. Fluorescence Polarization for Tie 2 Kinase

Final Assay Conditions:
  50 mM HEPES pH 7.5
  2% DMSO (when screening compounds)
  250 uM ATP
  2 mM MgCl$_2$
  1 mM DTT
  50 uM NaVanidate
  10 uM peptide substrate
  activated tie 2 kinase Peptide Substrate:
  RFWKYEFWR-OH
  MW (TFA salt)=1873 Da
  Make a 1 mM peptide stock and store at −20° C.
  Dilute to 100 uM just prior to use.

9× Kinase Buffer:
  450 mM HEPES pH 7.5
  900 mM NaCl
  450 uM NaVanidate
  18 MM MgCl$_2$
  100 mM DTT
  Can be made up ahead of time and stored in aliquots at −20° C.

ATP Stock:
  Make a 25 mM ATP stock and store in aliquots at −20° C. until needed. Dilute to 2.5 mM prior to use.

Activation of Tie 2 Kinase:
  Final Buffer Conditions:
  20 mM Tris-HCl pH 7.5
  12 MM MgCl$_2$
  100 mM NaCl
  20 uM NaVanidate
  1 mM DTT
  300 uM ATP Procedure:
1. Incubate 5 uM tie 2 kinase in the 300 uM ATP and the buffering conditions described above.
2. Allow to incubate at 27° C. for 2 hours.
3. Add 2.5 ml of the incubated tie 2 kinase reaction mix to a NAP-25 desalting column (Pharmacia Biotech cat. no. 17-0852-02) pre-equilibrated in 20 mM Tris-HCl pH 7.5, 100 mM $NaCl_2$ to separate the ATP from the enzyme.
4. Elute the enzyme with 5.0 ml 20 mM Tris-HCl pH 7.5, 100 mM $NaCl_2$; the protein concentration should be 2.5 uM at this point.
5. Aliquot out the enzyme and store at −80° C. as soon as possible.

Procedure:
For a 50 ul reaction add the following to each well of a 96-well black half-area plate (Costar, cat# 3694)
1. 5 ul of test compound in 20% DMSO.
2. 5 ul 9× kinase buffer.
3. 5 ul 2.5 mM ATP.
4. 5 ul 100 uM peptide substrate.
5. 25 ul PTK detection mix (Panvera, P-2652, 50 ml—UK distributor is Cambridge Bioscience).
6. 5 ul activated tie 2 kinase (protocol below) diluted in 1× buffer to initiate the reaction.
7. Read polarization on an FP instrument cycling for 30–50 minutes in accordance with enzyme activity. IC50 can be determined from the % polarization using normal calculation methods.

Compounds of the invention have IC50s in 1 nanomolar–$10^4$ nanomolar range, typically in the 700–$10^4$ nanomolar range.

B. Measurement of Tie2 Receptor Signal Transduction

HEL cells (ATCC # TIB180) are cultured at between 1 and $5 \times 10^5$ ml in RPMI-1640 medium supplemented with 2 mM glutamine and 10% FBS as a suspension culture. Sixteen to thirty-six hours prior to an experiment, the necessary number of cells are passaged into 0.5% FBS/RPMI medium. On the day of an experiment, cells are harvested and resuspended at a density of $0.5–1.0 \times 10^7$ cells ml in 0.5% FBS RPMI and seeded at 2–3 ml/well in six well plates.

Alternatively, Human Umbilical Vein Endothelial Cells (HUVECs) (Clonetics—Walkersville, Md.) may be used for the assay. HUVECs between passages 2 and 12, are plated at $2 \times 10^5$ and $1 \times 10^6$ cells per well in a six well plate in supplemented EGM (Clonetics). After 24 hours the media is changed to EBM containing 3% BSA (Clonetics), and the cells are cultured overnight and used for assay the following day.

Cells are treated with inhibitory compounds at appropriate concentrations for 30–45 minutes. The contents of the wells are mixed briefly on a rocker (approx 30 seconds) and then incubated at 37° C. The cells are then treated with a source of native ligand, such as serum or fibroblast conditioned medium for 10 minutes.

At the end of 10 minute incubation period the plate is placed on ice. The cells are harvested and the media is removed. The cells are lysed in denaturing sample buffer (Invitrogen—Carlsbad, Calif.). The suspension is sonicated for 5 pulses at a medium setting and returned to ice. The phosphorylation state of the Tie2 receptor is determined by Western blotting and detection by an anti-phospho-Tie2 antibody, as detailed below (Harlow, E., and Lane, D. P., *Antibodies—A Laboratory Manual*, Cold Spring Harbor Laboratory Press: New York, 1988.). Thirty ul of the lysate are run on a 7% SDS/polyacrylamide gel. The gel is then transferred to a nitrocellulose or PVDF membrane as per the manufacturer's instructions for Western blotting.

The blots are washed with PBS/0.05% Tween-20 and then blocked with 3% BSA/PBS/Tween for 1 hour at room temperature. The blots are then incubated with 1 ug/ml anti-phospho-Tie2 antibody (SmithKline Beecham or GlaxoSmithKline) in PBS/0.05% Tween for 1 hour. The blot is then washed 4 times with PBS/Tween for 5 minutes each. The blot is incubated with an anti-mouse-HRP conjugate secondary antibody at the dilution recommended by the manufacturer, in PBS/Tween for 1 hour. The blot is washed in PBS/Tween, 4 times for 5 minutes each. After the last wash, the blot is developed by the ECL method (Amersham) or some equivalent.

Using a densitometer or graphics program (e.g. ImageQuant—Molecular Dynamics), each blot is scanned. The Tie-2 band is isolated and "boxed out" for each lane. The pixel volume or comparable measure for each sample is analyzed. Also, an appropriate background region of the same dimensions is determined for each sample. After adjusting for background, phosphorylation is expressed as the ratio of phosphotyrosine staining, relative to the untreated control. Reduced phosphorylation indicates inhibition of tie-2 kinase.

C. Measurement of Angiogenesis in vivo—Murine Air Pouch Granuloma Model

Described below is a model of inflammatory angiogenesis used to show that inhibition of Tie2 will stop the tissue destruction of excessive, inappropriate or undesirable proliferation of blood vessels. The murine airpouch granuloma model of chronic inflammation (Kimura et al., 1985, *J. Pharmacobio-Dyn.*, 8:393–400; Colville-Nash et al., 1995, *J. Pharm. and Exp. Ther.*, 274:1463–1472) whose disclosure is incorporated herein by reference in its entirety, is characterized by inflammatory cell influx, fibrous tissue proliferation and intense angiogenesis. It is representative of inflammatory angiogenesis and demonstrates that the angiogenic component can be pharmacologically modulated independently of granuloma growth and size. In addition, angiogenesis can be accurately quantitated by a vascular casting method.

Day −1, mice are anesthetized using Aerrane (isoflurane) gas (5%) or other approved methods, after which 3 mls of air is injected into the dorsal subcutaneous tissue using a 27 g needle. Mice are allowed to recover.

Day 0, mice are again anesthetized using Aerrane or other approved methods, once anesthetized 0.5 ml of Freunds complete adjuvant with 0.1% v/v croton oil is injected into the air pouch formed on Day −1. The animals also begin their dosing regime (number of days dependent upon study) with the animals typically receiving compound in 0.2 ml N,N, Dimethyl Acetoacetamide(DMA) (Sigma, St. Louis, Mo.)/Cremephor E1 (Sigma, St. Louis, Mo.), saline (10/10/80) or other appropriate vehicle. The animals are allowed to recover and all subsequent dosing is performed on the animals in the absence of anesthetics.

Days 1–5, animals are dosed according to schedule.

On Day 6 the animals are again anesthetized after which a vascular cast is made (Kimura et al., 1986, *J. Pharmacobio-Dyn.*, 9:442–446); this involves a 1 ml tail vein i.v. injection of a Carmine Red (10%) (Sigma, St. Louis, Mo.)/gelatin (5%) (Sigma, St. Louis, Mo.) solution. The animals are then sacrificed by lethal dose of anesthesia and chilled at 4° C. for 2 hours prior to the removal of the granuloma tissue.

When the granuloma is removed it is weighed and then dried for 3 days at 45° C. and reweighed. The dried tissue is then digested in 0.9 ml of a 0.05M phosphate buffer pH 7.0 containing 12 U/ml$^{-1}$ papain (Sigma, St. Louis, Mo.) and 0.33 g/L$^{-1}$ N-acetyl-1-Cysteine (Sigma, St. Louis, Mo.) at 57° C. for 3 days. After 3 days digestion the carmine red is solublized by the addition of 0.1 ml 5 mM NaOH. Samples are centrifuged and then filtered using 0.2 um acrodiscs. The carmine content is then determined against a carmine red standard curve (0.5 to 2 mg/ml) generated in extracted tissue from non carmine treated animals and read at 490 nm. Sample and standard values are determined typically using DeltaSoft Elisa analysis software (Biometallics Inc., Princeton, N.J.). The carmine content is then used to determine the vascular indexes for the various treatments, vascular index being the mg carmine dye/gm dry tissue.

The effect of compounds on vascular density is typically measured 6 days after induction of the granuloma. This time point has been determined to be at or near the peak of angiogenesis. As a positive control medroxyprogesterone, an angiostatic steroid (Gross et al., 1981, Proc. Natl. Acad. Sci. USA, 78:1176–1180), whose disclosure is hereby incorporated by reference in its entirety, is utilized. This control demonstrates a maximum reduction of 50% in this model. Medroxyprogesterone has no effect on granuloma size as measured by dry weight.

D. Measurement of Angiogenesis in vivo—Matrigel Model

Angiogenesis is modeled in-vivo by placing an extracellular matrix gel, beneath the skin of a mouse for approximately one week, and then employing several measures to quantitate angiogenic invasion of the gel (Biancone, L, et.al. Development of Inflammatory Angiogenesis by Local Stimulation of Fas In Vivo. J. Exp. Med. 186:147, 1997.). Briefly, reduced growth factor, endotoxin free Matrigel® (Becton-Dickinson, Bedford, Mass.) is a gel at low temperatures. Antibodies or known angiogenic agents are mixed with the gel, such that they do not constitute more than 2% of the total volume. Eight week old or older, C57 female mice are administered 0.5 ml of the Matrigel® by dorsal subcutaneous injection through chilled syringes. At physiological temperature, the liquid matrigel® rapidly forms a solid and cohesive gel. During the course of the experiment, mice receive test compounds or controls administered as described above. After six days, the mice are sacrificed and the Matrigel® plugs recovered. Angiogenesis is quantitated by analyzing the hemoglobin content of the gel by the method of Drabkin (Drabkin, D L and Austin, J H: Spectrophotometric Studies II. Preparations from washed blood cells; nitric oxide hemoglobin and sulfhemoglobin. J Biol Chem 112:51, 1935.)(Sigma, St. Louis, Mo.), or by staining and quantitating blood vessels with CD31 staining as described above.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound of formula (I), or a pharmaceutically acceptable salt, solvate, or hydrate thereof

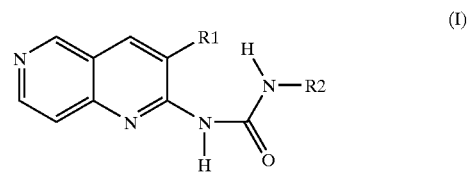

wherein:
R1 is selected from the group consisting of aryl, aralkyl, heteroaryl, heteroarylalkyl, heterocyclic, heterocyclicalkyl, aroyl, and alkanoyl;
R2 is selected from the group consisting of H, C 1–10 alkyl, cycloalkyl, aryl, aralkyl, heteroaryl, heteroarylalkyl, heterocyclic, heterocyclicalkyl, alkenyl, cycloalkenyl, and alkynyl; and
wherein R1 and R2 may be independently optionally substituted, with one or more substituent selected from the group consisting of:
halogen;
hydroxy;
hydroxy substituted C1–10 alkyl;
C1–10 alkoxy;
S(O)$_m$ alkyl, wherein m is 0, 1 or 2;
amino;
mono-substituted amino;
di-substituted amino;
C1–10 alkyl;
cycloalkyl;
cycloalkyl alkyl;
halosubstituted C1–10 alkyl;
aryl or aralkyl wherein the aryl moieties may also be substituted one to two times by halogen, hydroxy, hydroxy substituted alkyl, C1–10 alkoxy, S(O)$_m$ alkyl, amino, mono-substituted amino, di-substituted amino, C1–10 alkyl, or halosubstituted C1–10 alkyl;
alkenyl; and
alkynyl.

2. A compound according to claim 1 wherein R1 is selected from the group consisting of aryl, substituted aryl, heteroaryl, and substituted heteroaryl.

3. A compound according to claim 1 wherein R1 is selected from the group consisting of phenyl, thiophene, pyridinyl, and pyrazole, which may be substituted or unsubstituted.

4. A compound according to claim 3 wherein R1 is substituted with one or more substituent selected from the group consisting of: $C_{1-10}$ alkyl, halo, halosubstituted $C_{1-10}$ alkyl, $C_{1-10}$ alkoxy, amino, mono-substituted amino, and di-substituted amino.

5. A compound according to claim 3 wherein R1 is substituted with one or more substituent selected from the group consisting of: methyl, fluoro, chloro, CF$_3$, methoxy, and dimethyl amino.

6. A compound according to claim 1 wherein R2 is selected from the group consisting of: C 1–10 alkyl, cycloalkyl, aryl, and heterocyclic, which may be substituted or unsubstituted.

7. A compound according to claim 1 wherein R2 is selected from the group consisting of: $C_{1-10}$ alkyl, cycloalkyl, substituted aryl, and heterocyclic.

8. A compound according to claim 1 wherein R2 is selected from the group consisting of: methyl, ethyl, tert-butyl, cyclohexyl, and tetrahydropyranyl.

9. A compound according to claim 1 wherein R1 is substituted phenyl and R2 is selected from the group consisting of $C_{1-10}$ alkyl, cycloalkyl, and heterocyclic.

10. A compound according to claim 9 wherein R2 is selected from the group consisting of $C_{1-4}$ alkyl, cyclohexyl, and tetrahydropyranyl.

11. A compound according to claim 10 wherein R1 is substituted with one or more substituent selected from halo and $C_{1-4}$ alkyl.

12. A compound selected from the group consisting of:
3-[2,6-dichlorophenyl]-1,6-naphthyridin-2'-2-[N'-(1,1-dimethylethyl)-urea]; 1-tert-butyl-3-[3-(2-chloro-6-fluoro-phenyl)-[1,6]naphthyridin-2-yl]-urea;
1-[3-(2-chloro-6-fluoro-phenyl)-[1,6]naphthyridin-2-yl]-3-(tetrahydro-pyran-2-yl)-urea;
1-tert-butyl-3-[3-(2,5-dimethyl-phenyl)-[1,6]naphthyridin-2-yl]-urea;
1-[3-(2,5-dimethyl-phenyl)-[1,6]naphthyridin-2-yl]-3-ethyl-urea; and
1-[3-(2,5-dimethyl-phenyl)-[1,6]naphthyridin-2-yl]-3-(tetrahydro-pyran-2-yl)-urea.

13. A pharmaceutical composition comprising an effective, non-toxic amount of a compound according to claim 1 and a pharmaceutically acceptable carrier or diluent.

14. A compound according to claim 4 wherein R1 is phenyl.

15. A compound according to claim 14 wherein R2 is selected from the group consisting of: methyl, ethyl, tert-butyl, cyclohexyl, and tetrahydropyranyl.

* * * * *